United States Patent [19]

Mangold et al.

[11] Patent Number: 5,296,356

[45] Date of Patent: Mar. 22, 1994

[54] ENZYME-IMMUNOASSAY METHOD FOR THE DETERMINATION OF AN ANALYTE

[75] Inventors: Dieter Mangold, Maxdorf; Ulrich Traeger, Limburgerhof; Hans Lange, Lampertheim, all of Fed. Rep. of Germany

[73] Assignee: Boehringer Mannheim GmbH, Mannheim, Fed. Rep. of Germany

[21] Appl. No.: 626,257

[22] Filed: Dec. 12, 1990

[30] Foreign Application Priority Data

Dec. 13, 1989 [DE] Fed. Rep. of Germany ..... 3941150.8

[51] Int. Cl.$^5$ ........................................... G01N 33/543
[52] U.S. Cl. ..................... 435/7.92; 435/7.93; 435/7.94; 435/7.95; 435/970; 436/518; 436/527; 436/529; 436/530; 436/531; 436/538; 436/541; 436/810; 422/56; 422/102
[58] Field of Search ...................... 422/56–60, 422/102; 435/7.9–7.95, 805, 810, 969, 970; 436/518, 523, 527–531, 538, 541, 810

[56] References Cited

U.S. PATENT DOCUMENTS

| | | | |
|---|---|---|---|
| 4,426,451 | 1/1984 | Columbus | 422/58 X |
| 4,446,232 | 5/1984 | Liotta | 436/531 X |
| 4,654,197 | 3/1987 | Lilja et al. | 422/56 |
| 4,729,875 | 3/1988 | Chandler | 422/58 |
| 4,743,536 | 5/1988 | Evanega et al. | 436/533 X |
| 4,786,594 | 11/1988 | Khanna et al. | 435/7.9 |
| 4,857,453 | 8/1989 | Ullman et al. | 436/514 X |
| 4,978,504 | 12/1990 | Nason | 422/58 X |

FOREIGN PATENT DOCUMENTS

| | | | |
|---|---|---|---|
| 286371 | 10/1988 | European Pat. Off. | 436/514 |
| 8808534 | 3/1988 | PCT Int'l Appl. | 435/970 |

OTHER PUBLICATIONS

Patent Abstracts of Japan vol. 8: NR159 (P. 289) 1596, Jul. 24, 1984.

*Primary Examiner*—Esther L. Kepplinger
*Assistant Examiner*—Carol A. Spiegel
*Attorney, Agent, or Firm*—Felfe & Lynch

[57] ABSTRACT

The invention concerns a method for the detection of an analyte in a sample liquid by an enzyme-immunoassay in which an enzyme-labelled compound is partitioned between a solid and a liquid phase and the amount of enzyme label in the liquid phase outside the solid phase is determined as a measure of the concentration of the analyte. The measurement is carried out in a non-porous molding having the liquid phase contained therein in contact with the solid phase. The method is particularly suitable for carrying out in a cuvette which can be filled via the porous matrix or on a test strip having a space in contact with the solid phase.

14 Claims, 1 Drawing Sheet

ENZYME-IMMUNOASSAY METHOD FOR THE DETERMINATION OF AN ANALYTE

SUMMARY

The subject matter of the invention is a method for the detection of an analyte in a sample liquid by a heterogeneous enzyme-immunoassay and a suitable test agent therefor.

DESCRIPTION

Figure 1:
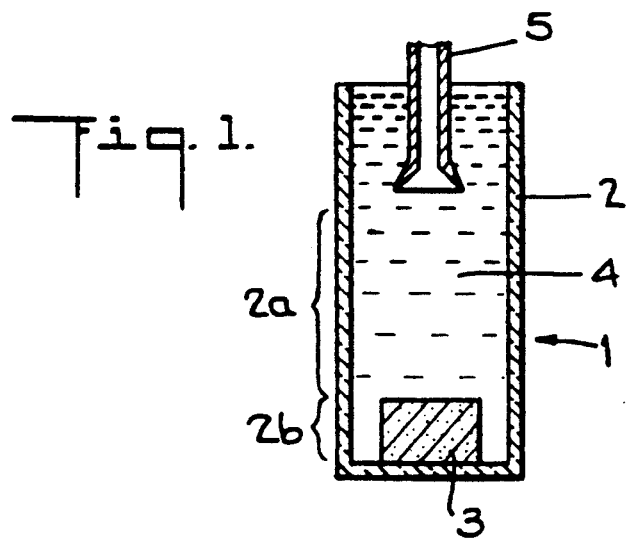
FIG. 1 shows a cross-section through the middle of a cuvette according to the present invention.

Enzyme-immunoassays are increasingly replacing the hitherto conventional radioimmunoassays. The use of enzymes to label immunologically reactive compounds in immunoassays has, in particular, technical advantages with regard to safety. Such an enzyme-immunoassay is described for example in U.S. Pat. No. 4,446,232. This procedure is based on the release of an enzyme-bound antibody from a first zone by the analyte contained in a sample and the enzyme label is visualized in a second zone by reaction with a suitable enzyme substrate. The first and the second zone consist of a porous material. It has, however, turned out that this procedure has the disadvantage that the colour formed cannot be measured by transmission photometry since the porous material of the second zone is barely transparent.

An enzyme-immunoassay is described in EP-A-0185372 (U.S. Pat. No. 4,820,644) in which, after the immunological reaction, the liquid is removed from the first zone by centrifugation and is then fed to a cuvette in which the colour reaction is then measured. Although the complete removal of the liquid from the porous material of the first zone has the advantage that this solid phase does not then interfere with the detection, the additional step which has to be carried out of completely separating the liquid from the solid phase is, however, disadvantageous.

Heterogeneous enzyme-immunoassays are often also carried out in so-called tubes. The smooth inside of the tubes then serves as the solid phase. These tube tests have the disadvantage that only a small amount of immunologically active substance via which the analyte could be immobilized is immobilized on the solid phase. In addition, the incubation times for such tests are very long. These tube tests also have the disadvantage that the incubation solution must be removed as completely as possible from the tube after the incubation since residues remaining in the tube influence the measurement.

The object of the present invention was to avoid the disadvantages of the state of the art and in particular to provide simpler, faster or more sensitive enzyme-immunoassays.

This object is achieved by the invention described in the following.

The subject matter of the invention is a method for the detection of an analyte in a sample liquid by an enzyme-immunoassay in which an enzyme-labelled compound is partitioned between a solid and a liquid phase and the amount of enzyme label in the liquid phase outside the solid phase is determined as a measure for the concentration of the analyte characterized in that the measurement is carried out in a non-porous moulding and the liquid phase Contained therein is in contact with the solid phase.

The method according to the present invention is an improved method based on the so-called heterogeneous enzyme-immunoassays known up to now. Such immunoassays are described for example in *Mitteilungen der Deutschen Gesellschaft Fur Klinische Chemie*, 5, page 291–302 (1986). The basis of all these enzyme-immunoassays is the use of enzyme-labelled immunologically-active compounds and a solid and a liquid phase. Immunologically-active compounds are immobilized on the solid phase witch react directly or indirectly, for example via the analyte to be determined, with the enzyme-labelled compound and can immobilize it. Depending on the test procedure, the immobilized immunologically-active compound is a component of an immunological reaction with the analyte or an analyte analogue or the analyte. The reaction can be carried out in such a way that only a part of the enzyme-labelled compound is immobilized or remains immobilized as a result of which a definite amount of the enzyme-labelled compound remains in the liquid phase and either the amount of enzyme label on the solid phase or in the liquid phase is a measure for the concentration of the analyte. In the method according to the present invention the amount of enzyme label is measured in the liquid phase.

All immunologically active compounds come into consideration as the analyte. Such compounds are components of an immunological pair or complex, in particular haptens, Antigens or antibodies.

A sample liquid is, in particular, understood as body fluids or fluids derived therefrom. Body fluids include, for example, blood or urine. Sample liquids derived from these fluids are, for example, those which can be obtained by dilution or concentration of these fluids or by addition or removal of particular components from the fluid, for example serum or plasma.

All materials with a large active surface are suitable as the solid phase within the scope of the invention. This includes all porous solids providing that they are capable of absorbing the liquids mentioned above and that these liquids can flow through them. Fleece and fabrics are particularly suitable. Suitable materials for the solid phase are known to the expert for example from U.S. Pat. No. 4,446,232. They also include cellulose and mixtures of cellulose and suitable plastics. The solid phase can also be a particulate solid phase. In addition this solid phase also contains an immobilized immunologically-active compound suitable for carrying out the enzyme-immunoassay which participates in the immobilization of the enzyme-labelled compound. It has turned out that tests with such solid phases are particularly well suited for rapid immunoassays.

An enzyme-labelled compound is a chemical comprising a component of an immunological reaction and an enzyme. The component of the immunological reaction is chosen from the group of haptens, antigens or antibodies and depends on the type of analyte and on the type of test procedure. In particular, hydrolases and enzymes catalysing redox reactions come into consideration as the enzyme for which substrates are available which allow a measurement of the enzyme activity. $\beta$-galactosidase and peroxidase have proven to be particularly suitable.

The measurement of the amount of enzyme label is carried out in a non-porous vessel after partitioning of the enzyme-labelled compound between the solid and the liquid phase. For this purpose, at least a portion of the liquid phase is removed from the pores of the solid phase and brought onto its surface. The liquid phase is then still in contact with the solid phase. The sample liquid is preferably displaced from the pores of the solid phase by a further liquid.

The amount of enzyme label is measured by monitoring a reaction of the enzyme with a suitable substrate. An advantage of an enzyme label and of carrying out a reaction with a suitable substrate is the high sensitivity of the resulting tests. The substrate is converted by the enzymatic reaction into a detectable compound or a detectable compound is released from it or a compound results the amount of which can be made detectable in a subsequent reaction. If the enzyme is a hydrolase, chromogenic or fluorogenic substrates can, for example, be used as disclosed in EP-A-0156347. The enzyme substrate can be added to the liquid phase, for example, in the non-porous moulding. The substrate is, however, preferably contained in the liquid which displaces the sample liquid from the porous material. In this case, the amount of displacing liquid used is, such that at least a portion of the liquid overflows into the non-porous moulding. The moulding can, for example, be the interior of a vessel such as a cuvette or a shallow space between two walls. An advantage of the use of a non-porous moulding is that the sensitivity is clearly increased. This applies in the case of a reflection photometric as well as of a transmission photometric measurement.

It is extraordinarily surprising that the enzyme label bound to the solid phase which is in liquid contact with a non-porous moulding does not interfere with the measurement in this moulding since the bound enzyme can indeed continuously release detectable material which can diffuse into the moulding.

Because the measurement is carried out in a non-porous moulding the determination can be carried out by transmission photometry. Compared to state-of-the-art test strips the measurement in a non-porous moulding has the advantage that it can be considerably more sensitive.

Figure 2:
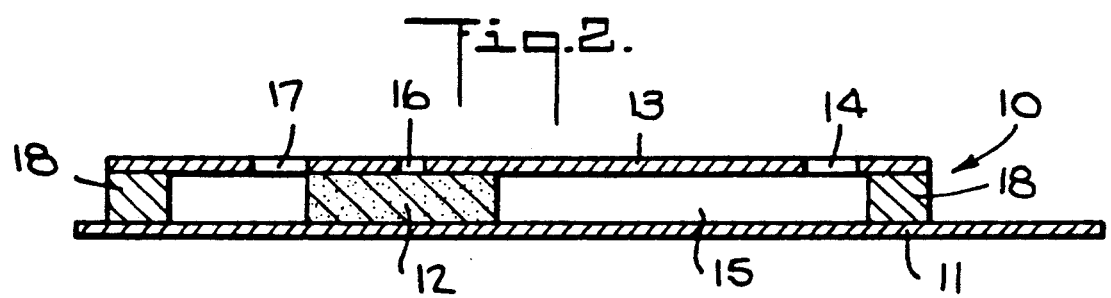
FIG. 2 shows a longitudinal section through the middle of a test strip according to the present invention.
Figure 3:
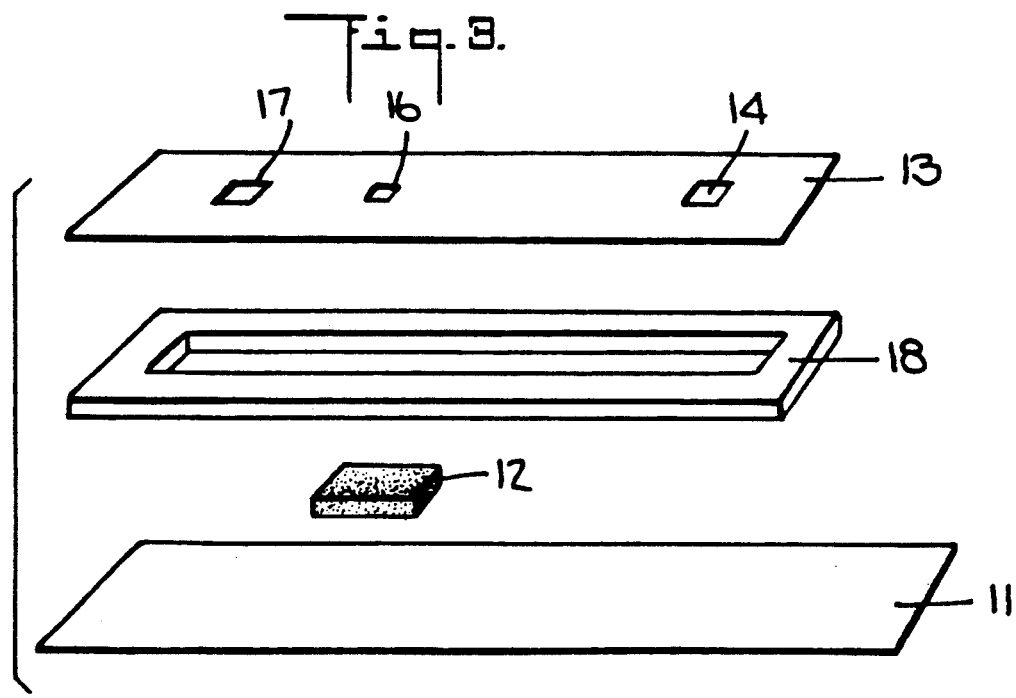
FIG. 3 shows the individual elements of a test strip of the present invention according to FIG. 2.

The method according to the present invention is particularly suitable for the detection of an analyte in a cuvette as shown in FIG. 1 or a test strip as in FIG. 2 (longitudinal section). FIG. 3 shows a process for the production of a test strip according to FIG. 2.

A preferred embodiment is described with the aid of FIG. 1. The device I consists of a cuvette 2 with an upper region 2a and a lower part 2b in which a porous material 3 (matrix) is fixed. It can be fixed by glueing the matrix to the cuvette or the matrix can be clamped into the cuvette. At least the part 2a of the cuvette is transparent to electromagnetic radiation, in particular to light of the wavelength which is required to determine the label. The sample and, if desired, auxiliary reagents are pipetted onto the porous material 3. The amount of liquid pipetted should preferably not exceed the saturation volume of the porous material.

After an incubation period during which the enzyme-labelled compound partitions between the porous solid matrix and the liquid phase, the device is filled through the matrix, for example with the aid of a needle 5 which is lowered onto the matrix. In this process the liquid phase contained in the pores of the matrix is virtually completely displaced from the matrix by the solution The displacing solution contains a substrate for the enzyme label.

After a second incubation period the colour development is measured in supernatant 4 (in region 2a). The colour development in the supernatant can, however, also be measured directly without a second incubation period by a kinetic measurement.

It is also possible to partially fill the device through the porous material with a buffer solution without substrate and subsequently to add substrate solution to the supernatant.

According to a further embodiment, the method according to the present invention is carried out in a test strip according to FIG. 2. The test strip 10 contains a porous matrix 12 on a base foil 11 which is at least partially covered by a foil 13. The foil 13 and the base foil 11 which are adjacent to the porous matrix 12 form a non-porous space of the vessel 15. This space preferably contains an air vent 14. The known inert plastic foils for test strips are suitable as the foil.

In order to carry out the method according to the present invention by means of the test strip 10, the sample liquid as well as, if desired, further reagents necessary for enzyme-immunoassays are applied to the porous matrix 12. This can, for example, be effected through a sample application aperture 16. After an incubation period the non-porous space of vessel 15 is filled through the porous, solid matrix 12 with a displacing fluid. For this, the displacing fluid can be filled via the filling inlet 17. The displacing fluid can already contain an enzyme substrate. The displacing fluid displaces the liquid phase from the matrix. The amount of enzyme label can be determined by measurement of the colour development in the non-porous cuvette-like space 15. For a measurement by remission photometry one of the foils 13 and 11 is transparent and the other reflects light. Both foils are preferably transparent for a measurement by transmission photometry. A measurement vertical to the plane of the drawing is also possible.

A test strip according to FIG. 2 can be produced by glueing together three foils and the solid matrix 12 according to FIG. 3.

In this case, the base foil 11 is reflecting or transparent, part of foil 18 has been punched out and is preferably thicker than the foils 11 and 13, preferably about as thick as the porous solid carrier 12. Foil 13 has a sample application aperture 16, a filling inlet 17 and an air vent 14.

The transport of the sample and of the displacing liquid can take place under pressure (tipping or pipetting) or by means of capillarity. In the latter case the cuvette should have a layer thickness of less than 1 mm between 11 and 13. The embodiment of the method according to the present invention in a test strip has the advantage that the reactions can be started by simple pipetting (also manually) and can also be evaluated visually.

The enzyme-immunoassays mentioned above can be adapted as follows to carry out the method according to the present invention.

1. Displacement Test

A conjugate of an enzyme and an immunological partner of the analyte is bound to the porous material via an immunocomplex with an analyte or an analyte analogue immobilized on the porous material. The incubation of the porous matrix with the sample leads to a partial detachment of the conjugate from the porous material into the liquid phase and binding to the freely mobile analyte. So the immobilized analyte or analyte analogue is displaced by the analyte. After displacement of the liquid phase out of the porous material the amount of the conjugate-analyte complex is measured in the liquid phase.

2. IEMA

The sample containing the analyte and an enzyme conjugate directed towards the analyte are pipetted onto the porous matrix after a pre-incubation if necessary. The matrix contains binding sites for the free conjugate. After the displacement of the liquid phase, the complex of analyte and conjugate is measured in the liquid phase.

3. Competitive Test

A limiting amount of an immunological partner of the analyte is fixed to the porous material. The sample containing the analyte and a conjugate of an analyte or analyte analogue and an enzyme in known concentration are pipetted onto the porous material. Analyte and conjugate compete for the binding sites of the porous material. After the displacement, the amount of conjugate is measured in the liquid phase.

In a further embodiment of a competitive test, antibodies to the protein moiety of a polyhapten are fixed to the porous material. A polyhapten is for example, a conjugate of $T_4$ and IgG. The polyhapten (with bound sample and in known concentration), the sample and the conjugate of antibodies (AB) and enzyme (known concentration) are pipetted onto the porous material. Polyhapten and sample compete for the conjugate. Polyhapten and polyhapten conjugate complex are bound to the porous material. The complex sample/conjugate in the liquid phase is measured after displacement.

4. Sandwich Test

Antibodies (AB 1) to the analyte are bound to the porous material. The sample containing the analyte and a conjugate of enzyme and an antibody to the analyte (known concentration) are pipetted onto the porous material. After the incubation period and displacement, the non-bound conjugate is determined in the liquid phase. An antibody AB 2 to the antibody AB 1 can also be bound to the porous material. The incubation is then with the sample, the conjugate and AB 1.

The reagents necessary for carrying out enzyme-immunoassays are known and can be used analogously in the method according to the present invention.

In particular, when carrying out an immunoassay on one of the test strips described above the enzyme label can also be replaced by a so-called direct label. Direct labels include, for example, dyes, fluorescent dyes, solid particles, in particular metal sols of gold or of non-metals or their oxides such as selenium or tellurium. Such direct labels and the production of labelled compounds with them are known to the expert. Even though when using these it is not necessary to completely separate the liquid phase from the solid phase and the tests using direct labels are more sensitive than measurements in a pad, the use of enzyme labels in the tests, however, opens the possibility of even higher sensitivities.

The invention is elucidated further by the following Examples:

EXAMPLE 1

Albumin Test

A device according to FIG. 1 was used to carry out this test. The cuvette 2 had a volume of 1 ml. A pad (80% polyester, 20% sulphite pulp, height 0.8 mm, length×breadth 1 cm×0.5 cm, absorptivity 800 ml/m$^2$) onto which albumin was fixed according to DE-A-38 42 700 served as the porous matrix. 200 mU of a conjugate of an antibody to albumin and $\beta$-galactosidase is bound via an immunocomplex to the immobilized albumin. 20 $\mu$l sample liquid containing albumin is pipetted onto the pad material. After 5 min the device is filled via the pad material with a solution of chlorophenolred-$\beta$-D-galactoside (concentration 3 mmol, Hepes 50 mmol pH 7.5, amount 1 ml). After a further 5 min the absorbance is measured in the supernatant in a conventional photometer at 570 nm.

A calibration curve with sample liquids of known albumin content is established for the quantitative determination of albumin in urine. The result is shown in Table 1.

TABLE 1

| Analyte | concentration | Signal |
|---------|---------------|--------|
| 0 | mg albumin/dl | 203 mA |
| 1 | mg albumin/dl | 652 mA |
| 10 | mg albumin/dl | 880 mA |

The albumin concentration in urine samples of unknown albumin content can be determined using this calibration curve.

EXAMPLE 2

$T_4$ Test

A device according to FIG. 1 is used to carry out this test. $T_4$ is bound to a pad material (80% polyester, 20% sulphite pulp strengthened with etadurine) according to EP-A-0185372. After a pre-incubation of at least 5 min, 5 $\mu$l sample are pipetted onto the pad with 15 $\mu$l of a solution of a conjugate of AB to $T_4$ and $\beta$-galactosidase (3 U/ml). After 5 min the device is filled through the pad with a solution of chlorophenolred-$\beta$-D-galactoside (3 mM, 50 mmol Hepes pH 7.5) using a needle which is lowered onto the pad. The absorbance the supernatant is measured after 5 min at different $T_4$ concentrations in order to establish a calibration curve. The results are included in Table 2.

TABLE 2

| $T_4$ concentration | Signal |
|---------------------|--------|
| 0.8 $\mu$g/dl | 134 mA |
| 8.5 $\mu$g/dl | 585 mA |
| 25.1 $\mu$g/dl | 970 mA |

The $T_4$ content in serum or plasma can be determined using this calibration curve.

EXAMPLE 3

TSH Test

The test was carried out in a device according to FIG. 1. An antibody to mouse Fc analogous to U.S. Pat. No. 4,803,171 is fixed to the pad material (80% polyester, 20% sulphite pulp, etadurine). 425 $\mu$l standard (composition analogous to the TSH concentrations of Table 3) or sample, 80 $\mu$l antibody (mouse) to TSH (AB 1, 150 $\mu$g per ml) and 80 $\mu$l of a conjugate of sheep antibody to TSH and β-galactosidase (75 mU per ml) are pre-incubated for 120 min in a vessel. 20 µl of this solution is pipetted onto the pad material. After 5 min the device is filled through the pad with a solution of chlorophenolred-β-D-galactoside (concentration 3 mM, 50 mM Repes pH 7.5) using a needle which is lowered onto the pad material. The absorbance of the supernatant in the region 2a is measured after 5 min at different TSH concentrations. The calibration curve of Table 3 was obtained from this.

TABLE 3

| TSH concentration | Signal |
| --- | --- |
| 0 µU/ml | 760 mA |
| 31 µU/ml | 435 mA |
| 47 µU/ml | 330 mA |

An unknown concentration of TSH in serum or plasma can be determined using the calibration curve.

It will be understood that the specification and examples are illustrative but not limitative of the present invention and that other embodiments within the spirit and scope of the invention will suggest themselves to those skilled in the art.

We claim:

1. Method for determining an analyte in a liquid sample by an enzyme immunoassay comprising:
   (a) providing a transparent nonporous vessel comprising therein a porous solid phase having immobilized thereon a specific binding partner selected from the group consisting of a first specific binding partner which specifically binds to the analyte, the analyte, and an immunologically reactive analogue thereof;
   (b) providing an enzyme-labelled immunologically active compound comprising an enzyme label conjugated to a compound selected from the group consisting of the analyte, the immunologically reactive analogue thereof and a second specific binding partner which specifically binds to the analyte or the immunologically reactive analogue thereof as either
      (1) a separate liquid reagent or
      (2) as part of the porous solid phase, wherein the enzyme-labelled immunologically active compound is specifically bound to the specific binding partner on the porous solid phase;
   (c) contacting the liquid sample with both the enzyme-labelled immunologically active compound and the immobilized specific binding partner such that the liquid sample and the enzyme-labelled immunologically active compound form a first liquid phase wherein no more liquid volume is contacted than can be maximally absorbed by the porous solid phase and for a time sufficient for the enzyme-labelled immunologically active compound to partition between the porous solid phase and the first liquid phase;
   (d) contacting the porous solid phase of step (c) with a liquid chromogenic substrate specific for the enzyme label in a volume sufficient to displace the first liquid phase and to form a second liquid phase above the porous solid phase in the transparent nonporous vessel; and
   (e) measuring the amount of chromogen produced in the second liquid phase in order to determine the amount of the analyte in the liquid sample, wherein the measurement is carried out in the transparent nonporous vessel of step (d) without prior removal of the porous solid phase.

2. The method of claim 1 wherein the contacting step (c) comprises directly contacting the liquid sample with the enzyme-labelled immunologically active compound specifically bound to the specific binding partner on the porous solid phase to form the first liquid phase thereon.

3. The method of claim 1 wherein the porous solid phase is a fleece or a fabric matrix.

4. The method of claims 1 or 2 wherein the porous solid phase is a particulate matrix.

5. The method of claims 1 or 2 wherein the transparent nonporous vessel is a cuvette and the porous solid phase is attached to the bottom of the cuvette.

6. The method of claims 1 or 4 wherein the measuring step is performed using transmission photometry.

7. The method of claim 1 wherein the enzyme-labelled immunologically active compound of step (b) is provided as a separate liquid reagent.

8. The method of claim 7 wherein the transparent nonporous vessel is a cuvette.

9. The method of claim 1 wherein the porous solid phase is a fleece matrix.

10. The method of claim 1 wherein the analyte is albumin, $T_4$ or TSH.

11. The method of claim 1 wherein the contacting step (c) comprises first contacting the liquid sample with the enzyme-labelled immunologically active compound provided as a separate liquid reagent to form a first liquid phase, and contacting the first liquid phase with the porous solid phase.

12. Method for determining an analyte in a liquid sample by an enzyme immunoassay comprising:
   (a) providing a test strip comprising
      1) a bottom foil,
      2) a porous solid phase carrier having immobilized thereon the analyte or an immunologically reactive analogue thereof or a specific binding partner which specifically binds to the analyte or the immunologically reactive analogue thereof, said carrier being attached to a portion of the bottom foil,
      3) an upper foil covering said bottom foil and said porous solid phase carrier, wherein a portion of said bottom foil and of said upper covering foil which is adjacent to the porous solid phase carrier form a non-porous space and wherein said upper covering foil has at least one opening for applying fluid to said porous solid phase carrier and at least one opening over the non-porous space;
   (b) providing an enzyme-labelled immunologically active compound comprising an enzyme label conjugated to a compound selected from the group consisting of the analyte, the immunologically reactive analogue thereof, and a second specific binding partner which specifically binds to the analyte and the immunologically reactive analogue thereof as either
      (1) a separate liquid reagent or
      (2) as part of the porous solid phase carrier, wherein the enzyme-labelled immunologically active compound is specifically bound to the specific binding partner on the carrier;
   c) contacting the liquid sample with both the enzyme-labelled immunologically active compound and the immobilized specific binding partner on the carrier such that the liquid sample and the enzyme-labelled immunologically active compound form a first liquid phase wherein no more liquid volume is contacted with the carrier than can be maximally absorbed by the carrier;

d) contacting a liquid chromogenic substrate for the enzyme label to the porous solid phase carrier in sufficient volume to displace unbound enzyme-labelled immunologically active compound from the carrier into the non-porous space of the test strip; and e) measuring the amount of chromogen produced in the non-porous space in order to determine the amount of the analyte in the liquid sample.

13. The method of claim 12 wherein the measuring step is performed by transmission photometry and wherein at least one of the bottom base foil and the upper covering foil are transparent.

14. The method of claim 12 wherein the measuring step is performed by transmission photometry and both the bottom base foil and the upper covering foil are transparent.

* * * * *

UNITED STATES PATENT AND TRADEMARK OFFICE
CERTIFICATE OF CORRECTION

PATENT NO. : 5,296,356
DATED : March 22, 1994
INVENTOR(S) : Dieter Mangold, et al.

It is certified that error appears in the above-indentified patent and that said Letters Patent is hereby corrected as shown below:

On title page, item [30]      change "394 11 508" to --3941150--

Col. 2, line 3:      change "Contained" to -- contained --.

Col. 2, line 14:     change "witch" to -- which --.

Col. 2, line 34:     change "Antigens" to -- antigens --.

Signed and Sealed this

Eighteenth Day of October, 1994

Attest:

BRUCE LEHMAN

*Attesting Officer*     *Commissioner of Patents and Trademarks*